United States Patent
Liungman

(10) Patent No.: US 9,993,622 B2
(45) Date of Patent: Jun. 12, 2018

(54) ASSEMBLY WITH A GUIDE TUBE, A FIXATOR FOR ATTACHING TO A BLOOD VESSEL, AND A PUMP

(71) Applicant: Endovascular Development AB, Uppsala (SE)

(72) Inventor: Krister Liungman, Uppsala (SE)

(73) Assignee: Endovascular Development AB, Uppsala (SE)

( * ) Notice: Subject to any disclaimer, the term of this patent is extended or adjusted under 35 U.S.C. 154(b) by 479 days.

(21) Appl. No.: 14/401,488

(22) PCT Filed: May 15, 2013

(86) PCT No.: PCT/EP2013/060080
§ 371 (c)(1),
(2) Date: Nov. 14, 2014

(87) PCT Pub. No.: WO2013/171276
PCT Pub. Date: Nov. 21, 2013

(65) Prior Publication Data
US 2015/0126965 A1  May 7, 2015

Related U.S. Application Data

(60) Provisional application No. 61/647,980, filed on May 16, 2012.

(51) Int. Cl.
*A61M 31/00* (2006.01)
*A61M 25/04* (2006.01)
*A61M 25/06* (2006.01)

(52) U.S. Cl.
CPC ........ *A61M 25/04* (2013.01); *A61M 25/0662* (2013.01); *A61M 2025/0681* (2013.01)

(58) Field of Classification Search
CPC .............. A61M 25/04; A61M 25/0662; A61M 2025/0681
(Continued)

(56) References Cited

U.S. PATENT DOCUMENTS 3,592,183 A   7/1971  Watkins et al.
4,661,094 A   4/1987  Simpson
(Continued)

FOREIGN PATENT DOCUMENTS

CN   2768675 Y   4/2006
EP   1149566 A2  10/2001
(Continued)

OTHER PUBLICATIONS

Arun Ranchod, "Novel Catheter for Focused Delivery of an Agent", MEDRAD Performance. For life., 2 pages.
(Continued)

*Primary Examiner* — Edelmira Bosques
(74) *Attorney, Agent, or Firm* — Harness, Dickey & Pierce, P.L.C.

(57) ABSTRACT

A fixator assembly comprising a fixator for fixing inside a blood vessel, a guide tube attached to the fixator and a pump for supplying a liquid to the blood vessel or from the blood vessel via the guide tube. Blood flow past the fixator is possible during pumping so that critical situations are avoided. A method of providing a liquid to a blood vessel using the assembly is also claimed. Sampling or liquid dosing thus may be performed during extended periods of time while performing this at a well-defined position in the blood vessel and potentially close to or at the desired position in the person.

20 Claims, 8 Drawing Sheets

(58) Field of Classification Search
USPC .......................................................... 604/509
See application file for complete search history.

(56) References Cited

U.S. PATENT DOCUMENTS

| | | | |
|---|---|---|---|
| 4,689,041 | A | 8/1987 | Corday et al. |
| 4,921,483 | A | 5/1990 | Wijay et al. |
| 5,152,277 | A | 10/1992 | Honda et al. |
| 5,181,911 | A | 1/1993 | Shturman |
| 5,256,141 | A | 10/1993 | Gencheff et al. |
| 5,370,617 | A | 12/1994 | Sahota |
| 5,439,445 | A | 8/1995 | Kontos |
| 5,509,900 | A | 4/1996 | Kirkman |
| 5,649,941 | A | 7/1997 | Lary |
| 5,687,718 | A | 11/1997 | Fischer et al. |
| 5,695,519 | A | 12/1997 | Summers et al. |
| 5,700,243 | A | 12/1997 | Narciso, Jr. |
| 5,746,709 | A | 5/1998 | Rom et al. |
| 5,769,870 | A | 6/1998 | Salahieh et al. |
| 5,833,659 | A | 11/1998 | Kranys |
| 5,947,889 | A | 9/1999 | Hehrlein |
| 6,245,012 | B1 | 6/2001 | Kleshinski |
| 6,336,934 | B1 | 1/2002 | Gilson et al. |
| 6,485,501 | B1 | 11/2002 | Green |
| 6,511,496 | B1 | 1/2003 | Huter et al. |
| 6,540,768 | B1 | 4/2003 | Diaz et al. |
| 6,558,405 | B1 | 5/2003 | McInnes |
| 6,652,554 | B1 | 11/2003 | Wholey et al. |
| 2001/0012951 | A1 | 8/2001 | Bates et al. |
| 2001/0031907 | A1 | 10/2001 | Downey et al. |
| 2001/0041909 | A1 | 11/2001 | Tsugita et al. |
| 2001/0044598 | A1 | 11/2001 | Parodi |
| 2001/0044634 | A1 | 11/2001 | Don Michael et al. |
| 2002/0022858 | A1 | 2/2002 | Demond et al. |
| 2002/0103501 | A1 | 8/2002 | Diaz et al. |
| 2002/0111648 | A1 | 8/2002 | Kusleika et al. |
| 2002/0123766 | A1 | 9/2002 | Seguin et al. |
| 2002/0128973 | A1 | 9/2002 | Kranzley et al. |
| 2002/0156456 | A1 | 10/2002 | Fisher |
| 2002/0156499 | A1 | 10/2002 | Konya et al. |
| 2002/0193825 | A1 | 12/2002 | McGuckin et al. |
| 2003/0004539 | A1 | 1/2003 | Linder et al. |
| 2003/0009189 | A1 | 1/2003 | Gilson et al. |
| 2003/0078614 | A1 | 4/2003 | Salahieh et al. |
| 2003/0181943 | A1 | 9/2003 | Daniel et al. |
| 2003/0233117 | A1 | 12/2003 | Adams et al. |
| 2004/0010280 | A1 | 1/2004 | Adams et al. |
| 2004/0073238 | A1 | 4/2004 | Makower |
| 2004/0073253 | A1 | 4/2004 | Morrill et al. |
| 2004/0153118 | A1 | 8/2004 | Clubb et al. |
| 2004/0260308 | A1 | 12/2004 | Gilson et al. |
| 2005/0187578 | A1 | 8/2005 | Rosenberg et al. |
| 2005/0203569 | A1* | 9/2005 | Kusleika ............... A61F 2/01 606/200 |
| 2005/0234431 | A1 | 10/2005 | Williams et al. |
| 2006/0041244 | A1 | 2/2006 | Hohmann et al. |
| 2006/0155322 | A1 | 7/2006 | Sater et al. |
| 2006/0190025 | A1 | 8/2006 | Lehe et al. |
| 2006/0241675 | A1 | 10/2006 | Johnson et al. |
| 2007/0106330 | A1 | 5/2007 | Rosenberg et al. |
| 2007/0123925 | A1* | 5/2007 | Benjamin ......... A61M 25/0041 606/194 |
| 2007/0142858 | A1 | 6/2007 | Bates |
| 2007/0208367 | A1 | 9/2007 | Fiorella et al. |
| 2008/0172036 | A1* | 7/2008 | Stys ................. A61M 25/0662 604/525 |
| 2008/0188806 | A1 | 8/2008 | Cattaneo et al. |
| 2008/0188881 | A1 | 8/2008 | Chon |
| 2008/0214889 | A1* | 9/2008 | Saadat ............... A61B 1/00089 600/104 |
| 2008/0255606 | A1 | 10/2008 | Mitra et al. |
| 2008/0276485 | A1 | 11/2008 | Pucciani et al. |
| 2009/0048583 | A1 | 2/2009 | Williams et al. |
| 2009/0069789 | A1* | 3/2009 | Freyman ............... A61M 25/10 604/509 |
| 2009/0099594 | A1 | 4/2009 | Brady |
| 2009/0270964 | A1 | 10/2009 | Huetter et al. |
| 2010/0262219 | A1 | 10/2010 | Frimerman |
| 2011/0172607 | A1 | 7/2011 | Rosenberg et al. |
| 2012/0283644 | A1 | 11/2012 | Rosenberg et al. |
| 2013/0267991 | A1 | 10/2013 | Johnson et al. |

FOREIGN PATENT DOCUMENTS

| | | |
|---|---|---|
| EP | 1172073 A1 | 1/2002 |
| EP | 1733702 A2 | 12/2006 |
| EP | 1894593 A2 | 3/2008 |
| EP | 2433590 A2 | 3/2012 |
| GB | 2020557 A | 11/1979 |
| JP | H07532 | 1/1995 |
| WO | WO-9727897 A1 | 8/1997 |
| WO | WO-9940868 A1 | 8/1999 |
| WO | WO-2005077450 A2 | 8/2005 |

OTHER PUBLICATIONS

Christian Herdeg et al., "GENIE$^{tm}$ catheter for liquid local drug delivery", Euro Intervention, pp. 286-288, 2007, Europa Edition.
Noveste, Beta-Cath™ 5F System, 2 pages, 2002, Noveste Corporation.
International Search Report PCT/ISA/210 for International Application No. PCT/EP2013/060080 Dated Sep. 4, 2013.
Written Opinion of the International Searching Authority PCT/ISA/237 for International Application No. PCT/EP2013/060080 dated Sep. 4, 2013.

* cited by examiner

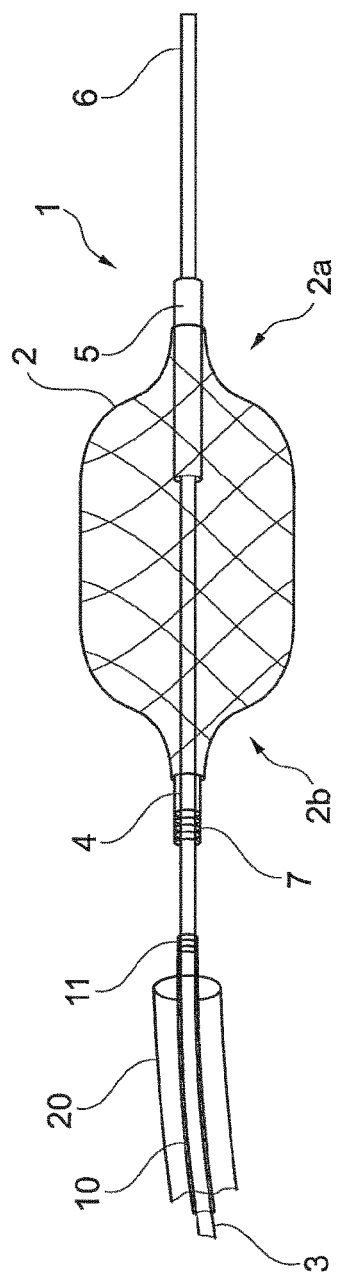
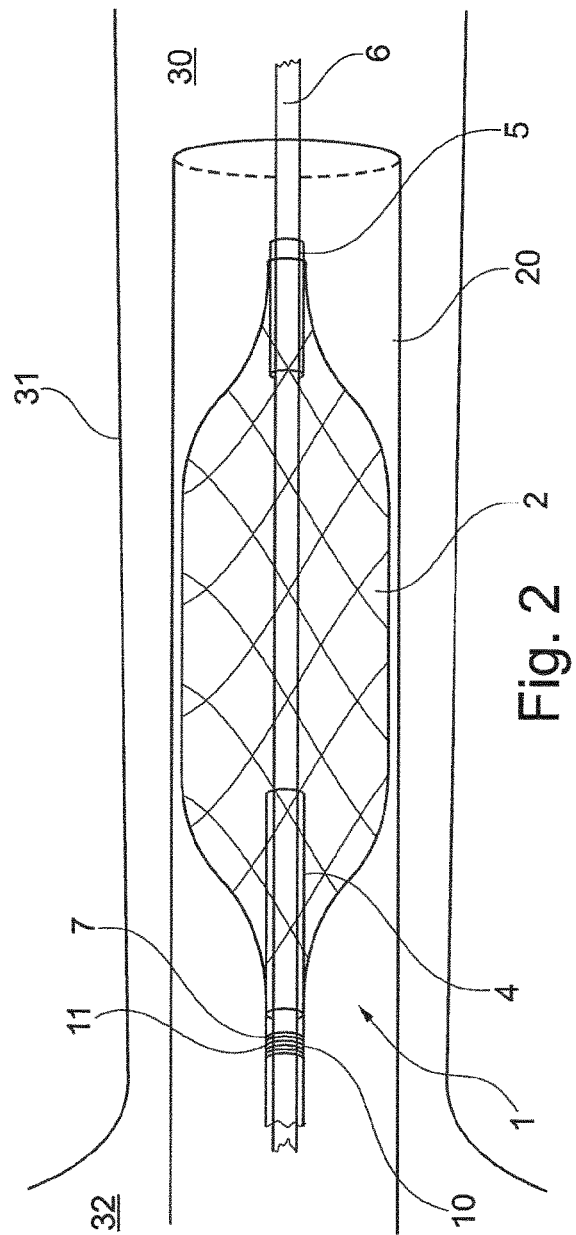

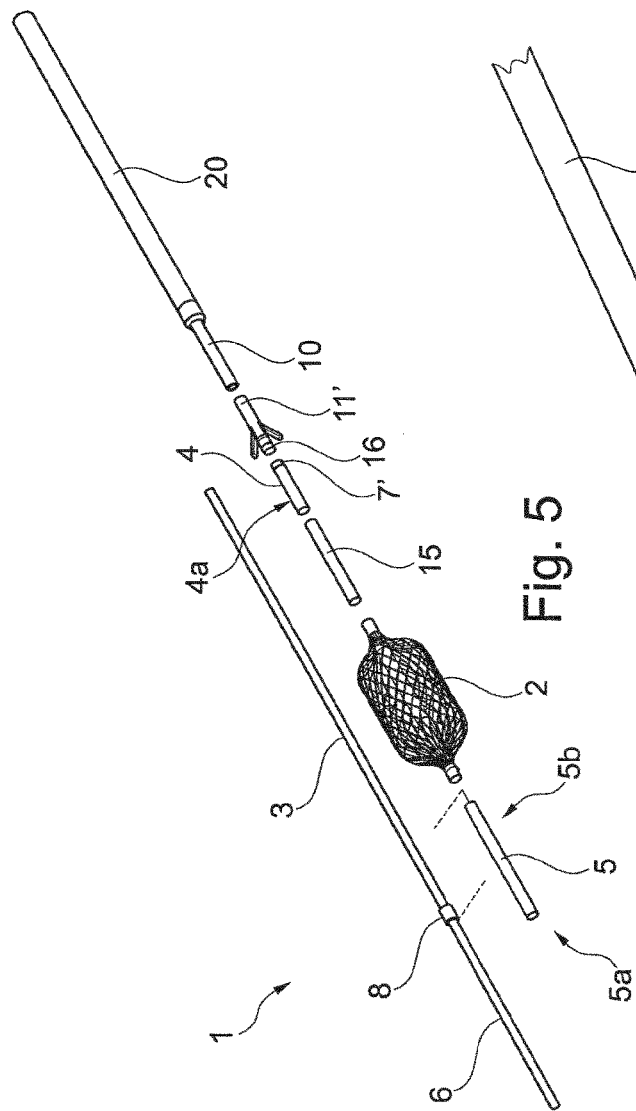
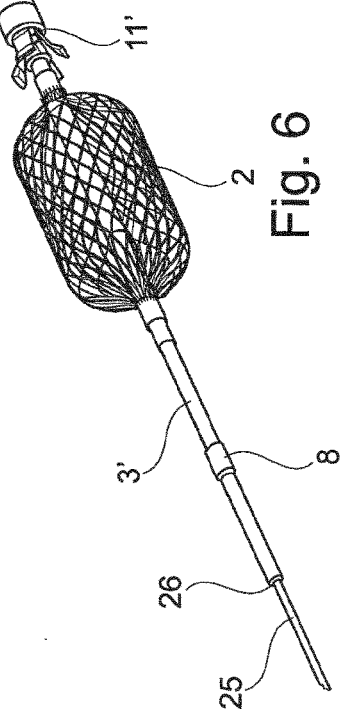

ASSEMBLY WITH A GUIDE TUBE, A FIXATOR FOR ATTACHING TO A BLOOD VESSEL, AND A PUMP

CROSS-REFERENCE TO RELATED APPLICATIONS

This application is the national phase under 35 U.S.C. § 371 of PCT International Application No. PCT/EP2013/060080 which has an International filing date of May 15, 2013, which claims priority to U.S. provisional patent application No. 61/647,980 filed May 16, 2012; the entire contents of each of which are hereby incorporated by reference.

The present invention relates to an assembly of a guide tube, a pump and a fixator or fixing element for attachment or fixing, preferably releasably, to the inner surface of a blood vessel inside e.g. a human being. This fixator is especially useful as it allows blood flow during its positioning in the blood vessel.

Elements of this type may be seen in:
http://www.bestvascular.com/assets/B-Cath %205F %20XL %20Delivery %20Catheter.pdf where simply the guide tube is provided without fixator,
http://www.medrad.com/en-us/resources/Documents/techpubs05-007.pdf where the guide tube is fixed using a balloon which also acts to actively stop blood flow during pumping of liquid,
http://www.medizin.uni-tuebingen.de/kardiologie/aktuelle/pdf/Oktober %202007%20Eurointervention %20.pdf where two balloons are used for generating a space for the drug while blocking blood flow.

A number of advantages are obtained when allowing blood flow during the operation of the pump, whether it be used for sample taking from within the blood vessel or for providing a liquid, such as a drug, to the blood vessel:
1. Uninterrupted blood flow maintains an undisturbed physiologic situation during blood sampling.
2. Maintaining the position in the target blood vessel over time allows repeated sampling to describe the time sequence of metabolic events in the tissue under investigation, e.g. in a malignant tumour, or in an endocrine tumour with hormonal release.
3. The use of the fixator will allow high concentration of drug delivered directly to the process under treatment, e.g. a malignant tumour without a first passage through the liver, and thus avoid consequent metabolisation of the pharmaceutical agent that potentially may reduce the drug effect.
4. The direct mode of delivery will allow repeated doses to be distributed timely in relation to biologic processes, such as e.g. cell regeneration in cancer treatment.
5. Treatment can be repeated for several days and weeks in a sequence.

In a first aspect, the invention relates to an assembly of:
a guide tube having a distal end for introduction into a blood vessel and a proximal end,
a fixator attached to the guide tube and being adapted to be releasably attached to an inner side of the blood vessel and
a pump for transporting a liquid to the blood vessel through the guide tube or from the blood vessel through the guide tube,
the fixator being adapted to allow blood flow in the blood vessel during transport of liquid to/from the blood vessel.

Presently, a guide tube is an elongated element adapted to be introduced into a blood vessel of a person. Often, a guide tube has a slippery surface, such as a hydrophilic surface, so as to be introduced into the blood vessel without harming the vessel. Typical guide tubes for catheterization have a circumference of between 0.14 and 0.89 mm. However, any thickness may in principle be used. The guide tube may be made of a polymer or a metal/alloy, such as nitinol.

The guide tube may be of a type having an outer sleeve which is rather pliable and an inner, stiffer, element which may be introduced into the sleeve, when the guide tube is desired more stiff and which may be withdrawn, when the guide tube is desired more pliable. In this manner, the higher stiffness may be used for positioning and deploying the fixator, where after the "released" lumen may be used for the liquid transport.

In this context, the distal end of the guide tube is that intended to be introduced into the blood vessel, whereas the proximal end is normally intended to extend out of the person.

Any type of pump may be used, and any type of liquid may, if desired, be transported into the blood vessel. The pump may be operated or operable manually or using a pump mechanism controlled by hydraulics, electronics, mechanics or the like. The pump may be operated or operable continuously, intermittently and/or when instructed by an operator or the like. The pump may be a piston pump, centrifugal pump, hose pump or may be based on any other type of technology. A liquid to be transferred into the blood vessel may be provided in a reservoir from which the pump may withdraw it for transport via the guide tube.

Any type of liquid may be withdrawn from the blood vessel. A filter may be provided at the distal end to prevent e.g. blood cells or other cells from entering the guide tube, or the like. Again, the withdrawal of the sample may be performed continuously, intermittently or when instructed by an operator, and the sample derived may be provided into one or more reservoirs or directly to analysis equipment, if desired. In one embodiment, a processor is adapted to control analysis equipment and the pump and to operate the pump on the basis of results of an earlier analysed, derived sample.

Naturally, the fixator may be introduced or be introducible into any blood vessel of a person or animal. Usually, the present fixator is for use in arteries of the person/animal, such as the aorta or one of the arteries directly receiving blood from the aorta, but this is not a limitation.

In the present context, the fixator may engage or attach itself to the inner side of the blood vessel in any desirable manner. A preferred manner is a friction attachment by which the fixator purely by friction attaches the blood vessel and thereby counteracts removal thereof along the axis of the blood vessel. A typical manner of obtaining a friction engagement is to provide a collapsible fixator inside the blood vessel in the collapsed form and allow it to expand so as to contact the inner side of the blood vessel. Usually, the expanding fixator will expand to be limited by the inner dimensions of the blood vessel so as to exert a predetermined force to the inner side of the blood vessel to stay in place.

Naturally, also other manners of engaging or attaching to the blood vessel are known, such as stent grafts with small spikes/hooks or nails which travel into the blood vessel wall in order to maintain or fix the element in the desired position.

In the present context, the fixator may be adapted to allow the blood flow in a number of manners. In one embodiment, the fixator may allow blood flow around it, such as if it does not engage the blood vessel along a complete circle. One example is a fixator defining at its outer contour, one or more ridges in which the blood may flow and thereby pass the fixator. In a preferred embodiment, however, the fixator will allow blood to flow there through while fixing to the vessel wall. This is described in more detail below.

In a preferred embodiment, the fixator comprises:
a deformable portion having a central portion adapted to attach to the inner side of the blood vessel at a predetermined length thereof, along a first longitudinal direction of the blood vessel, and
a connecting part attached to the deformable portion and the guide tube.

Firstly, the central portion will usually be those parts of the fixator which extend or are adapted to extend the farthest from a central longitudinal axis of the fixator. Usually, the blood vessels are tubular with a circular cross section at least locally around the fixator, so that the central portion normally is a tubular portion positioned the farthest from the central axis. As will be described further below, this tubular portion need not have the same cross section along its entire length.

Preferably, the predetermined length is between 2 mm and 30 mm, such as between 3 mm and 20 mm, preferably between 5 and 20 mm, such as between 10 and 16 mm.

In one situation, the deformable portion forms a closed or unbroken surface adapted to engage, touch or attach to the blood vessel. In another situation, the deformable portion comprises openings or holes. The deformable portion of the latter situation may be more easily compressed and expanded and may be made of a weave or braided element. The openings or holes of the deformable portion may have a cross section of between 0.01 mm$^2$ and 10 mm$^2$, such as between 0.1 mm$^2$ and 1 mm$^2$. The larger the openings, the lower will the contact surface between the weave/braided element be, but the more easily may the weave/braided element be compacted for introduction into the blood vessel.

Naturally, a transition or intermediate part may be present between the central portion and the connecting part at which transition a slight force may be exerted to the blood vessel wall. Such parts are not relevant in relation to the preferred embodiment, where the primary focus is to ensure that no local parts exist where an excessive force is applied.

The connecting part thus acts as a force transferring element connecting the guide tube and the deformable portion. This part may also be used for guiding the deformable portion during deployment and retraction from and into a delivery/removal catheter when desired.

In a preferred embodiment, the fixator is designed to cover a minimum cross sectional area across the blood vessel to not to any substantial degree disturb the blood flow through the fixator in the blood vessel, thus securing e.g. arterial supply to the end-organ, for example the kidney or the intestine.

One manner of determining a cross sectional area of the fixator is to project the fixator onto a plane perpendicular to the longitudinal axis of the blood vessel. In this manner, a measure of the cross section may be obtained, such as a percentage of the inner cross section of the blood vessel, but if e.g. a basket-type fixator of the type seen in FIG. 1 is used, this cross section will not be that actually seen by the flowing blood. This basket-type fixator will have a fixing part or deformable element engaging or attached to the blood vessel and which therefore is not relevant as to the cross section covered across the blood vessel cross section. However, this basket-type fixator may also have one end part (connecting part) or two end parts (proximal and distal parts; to be described further below) extending between the guide tube and the fixing part. These end parts will, when more than one is present, in the projection, be overlapping and thus give an erroneous measure for the cross section seen by the blood. In this situation, the cross section of that end part having the largest cross section is a better measure for the cross section seen by the blood. Preferably, the cross section(s) cover(s) less than 40%, such as less than 30%, preferably less than 20%, such as less than 10%, preferably less than 6% of the vessel cross section.

Thus, in one embodiment, the deformable portion defines, when projected on to a plane perpendicular to the longitudinal direction and in a rest position, a circumscribed portion with a first area and a cross section being less than 15% of the first area.

In this aspect, the rest position is a position in which no forces act on the deformable portion. In another embodiment, the same requirements may be put on the deformable portion when provided inside a blood vessel, as it is the amount of cross section taken up by the deformable portion in the blood vessel which defines the amount of blood flow allowed during actual use.

In this embodiment, the deformable portion takes up no more than 15% of the cross section. Preferably, this portion is even smaller, such as 10%, 5% or even less. In one embodiment, the deformable portion is a weaved tube engaging the blood vessel at its complete length so that virtually no blood flow reduction is generated by the deformable portion.

In that or another embodiment, the deformable portion defines, when projected on to a plane perpendicular to the longitudinal direction and in a rest position, a circumscribed portion with a first area and wherein the connecting part defines, when projected on to the plane and in the rest position, a cross section being less than 60% of the first area. The connecting part usually will extend across the direction of the blood flow from at or near the vessel wall to the guide tube. Again, it is desired that the blood flow reduction caused also by this part is reduced. A cross section of less than 60% is desired, but less than 50% is preferred, as is less than 30%, such as less than 20% or 10%.

Naturally, the whole fixator is interesting, so that it is preferred that the deformable portion defines, when projected on to a plane perpendicular to the longitudinal direction and in a rest position, a circumscribed portion with a first area and wherein the fixator defines, when projected on to the plane and in the rest position, a cross section being less than 75% of the first area, such as less than 60%, preferably less than 50%, such as less than 40%, preferably less than 30%, such as less than 20%.

One manner of making the connecting part able to allow blood flow during use is to have the connecting part comprise one or more strands of material extending from the deformable portion to the guide tube. The strands may be of any material, such as nitinol, and have any dimensions desired. The skilled person will known that the connecting part should be able to withstand deployment and possibly retraction of the fixator while providing a sufficient attachment between the guide tube and the deformable part to not detach during normal use. The strand(s) may be extending radially from the guide tube to the deformable element or may be weaved, such as to form a mesh, if desired. In addition a mesh of that type may be used as a filter for filtering detached material from vessel walls, if surgical procedures take place upstream of the position of the fixator.

In one embodiment, the connecting part, when projected on to a plane perpendicular to the longitudinal direction, defines a number of openings, at least 20% of the openings, such as at least 30%, 40%, 60% or 70% of the openings having a size exceeding 0.015 mm², such as exceeding 0.1 mm² or even exceeding 0.25 mm², such as exceeding 0.5 mm², or even exceeding 1 mm².

In one embodiment, the assembly further comprises:
preventing means engaging the guide tube and acting to prevent the fixator from travelling distally beyond the preventing means,
wherein:
the fixator is adapted to move toward the proximal end of the guide tube independently of the guide tube and
the fixator is adapted to maintain attachment to the inner side of the blood vessel, when a pulling force of at least 0.1N is applied to the guide tube and, via the preventing means, to the fixator.

When the fixator is prevented from travelling distally beyond the preventing means, it is ensured that the guide tube can not be pulled and thus separated from the fixator when the fixator is deployed and attached to the vessel. This preventing may be a fixing of the fixator to the guide tube. In that situation, the fixing will be detachable in order for the fixator to be movable proximally and independently of the guide tube and/or the preventing means. Alternatively, the fixator may be movable in relation to the guide tube and a stopping element may be provided preventing movement of the fixator beyond a predetermined point at the distal end. Naturally, part of the fixator may be allowed to travel distally of the preventing means, as long as one part thereof is not allowed to.

When the fixator is not in the fully deployed state, such as in a compressed state, it may be allowable to have the fixator independently movable in relation to the guide tube and/or preventing means, even though it may be desired to also in this situation or state prevent it from moving distally of the preventing means and/or the distal end of the guide tube, as it may then be lost in the blood vessel.

In one embodiment, the guide tube extends through a part of the fixator defining an aperture with predetermined inner dimensions, where the preventing means or stop has outer dimensions exceeding those of the aperture, so that the stop cannot move into and/or through the aperture. This stop may be a separate element fixed to the guide tube or an expanded part of the guide tube. Alternatively, a knot may be made on the guide tube.

In the present context, the fixator is able to move independently proximally of the guide tube and/or the preventing means so that it may be moved while the guide tube remains stationary. In fact, the fixator is preferably adapted to move along the guide tube. This is facilitated by the above structure where the fixator has an element encircling the guide tube, so that the guide tube extends through an aperture or the like of the guide tube. This has the advantage that the position of the fixator within the blood vessel is known (it is on the guide tube) even when it is not positioned or attached in the target blood vessel.

In order for the fixator to fulfil its function as a fixator, it preferably is able to maintain attachment to the inner side of the blood vessel, when a pulling force of at least 0.1N is applied to the guide tube and, such as via the preventing means, to the fixator. The function of the preventing means may be seen as to prevent the guide tube from fully detaching from the fixator, when the fixator is attached to the blood vessel and the proximal end of the guide tube is pulled.

The pulling of the guide tube may be intentional or non-intentional. Intentional pulling may be caused by re-direction of the guide tube or when directing additional elements into or toward the target blood vessel along the guide tube. Also, usually real-time imaging of the position of the fixator and other elements provided in the blood vessels of the person is performed, so that the identity or position of a fixator may be ascertained by pulling the proximal end or guide tube and identifying the fixator moving due to the pulling. Naturally, the fixator may move without detaching from the blood vessel. This detectable movement may be a slight sliding of the fixator within the blood vessel or simply the blood vessel moving as a result of the force exertion.

In the present context, the maintaining of the attachment is a movement of no more than than 1 mm of the fixator in relation to the blood vessel when the force is exerted in at least 10 seconds, such as at least 30 seconds, preferably at least 60 seconds. It is noted that no movement is desired, as any movement of the fixator while attached may cause damage to the blood vessel.

Depending on the type of surgical procedure and a number of other parameters, the fixator may be adapted to withstand a pulling force of more than 0.1N, such as 0.2N or more, preferably 0.3N or more, such as 0.4N or more, preferably 0.5N or more, such as 0.6N or more, preferably 0.7N or more, such as 0.8N or more, preferably 0.9N or more, such as 1N or more, preferably 1.5N or more, such as 2N or more, preferably 2.5N or more, such as 3N or more, preferably 3.5N or more, such as 4N or more, preferably 5N or more.

In the present context, the force which the fixator can withstand may be determined by testing the fixator in an animal blood vessel newly harvested from the animal and when immersed in saline. Blood vessels having diameters like those in human beings may be harvested from sheep, pigs, calves or cows. During the testing, the saline is not pumped through the vessel but kept more or less stand still. The force is exerted along a longitudinal axis of the blood vessel.

Clearly, a fixator will be adapted to be used in blood vessels of a given size or having a size within a specified diameter range. Thus, the testing should be performed under the same conditions, i.e. the fixator should be tested in a blood vessel having a size to which the fixator is prepared.

Naturally, the fixator may have a non-thrombogenic surface quality and flow promoting hydrodynamic design. Non-thrombogenic surfaces may be obtained by electro polishing the surfaces, for example.

In one embodiment, the deformable portion is adapted to exert at least substantially the same force to the blood vessel along all of the predetermined length when the pulling force of at least 0.1N is exerted to the guide tube and fixator.

Preferably, the deformable portion is adapted to exert at least substantially the same force to the blood vessel along all of the predetermined length when the pulling force of e.g. at least 0.1N is exerted to the guide tube and fixator.

In this context, the exerting of at least the same force along the predetermined length may mean that, along this length, the force exerted at all positions along the length will be within 20% of a mean value of the force exerted along the length, such as within 10% of the mean value, preferably within 5% of the mean value.

In another situation, the "at least the same force" may mean that, along the length, no position exists at which a force exceeding a mean value of the force exerted along the length by more than 20%, such as 10%, preferably 5% of the mean value. Naturally, a lower force exertion is a much smaller problem than an excessive force exertion.

Usually, the force exerted at a point along the direction will be the same around the circumference of the central portion at a given position along the direction. Thus, the force may be summed or integrated around the circumference for the individual points. If the force deviates more than e.g. 10% around this circumference, individual angular positions around the direction may also be taken into account in order to identify or prevent such force "peaks".

In that or another embodiment, the connecting part is a distal part attached to the deformable portion, the assembly further comprising a proximal part attached to the deformable portion and being translatable, along a second longitudinal axis, in relation to the distal part, the distal part being positioned closer to the distal end of the guide tube than the proximal part, the central portion of the deformable portion circumscribing, in a plane perpendicular to the second longitudinal axis, a larger cross section when a first distance exists between the proximal and distal parts compared to when a second distance exists between the proximal and distal parts, the second distance being larger than the first distance.

Preferably one or both of the distal and proximal parts is adapted to engage the guide tube and/or the preventing means. In a preferred embodiment, both the distal and proximal parts define apertures through which the guide tube is adapted to slide. Even more preferably, the preventing means is then fixed to the guide tube and is not able to travel through the aperture of one or both of the distal and proximal ends.

The discussion and function of the central/deformable portions and the distal/proximal parts may be as those described above.

The deformable portion circumscribes a cross section or a cross sectional area by the outermost parts of the deformable part defining this cross section or area. Naturally, the deformable part may comprise only a thin layer/weave or the like of material so that the overall cross section of the deformable portion is a narrow, closed curve, but it may also have an internal structure in order to keep the deformable portion expanded so as to attach to the blood vessel. One general, preferred type of deformable portion is a pre-shaped element automatically expanding when in the vessel. In this situation, no inner structure may be required to obtain the expansion.

In this context, the second longitudinal axis preferably may be an axis around which the deformable portion or the central portion is symmetric. Also, it may be desired that the proximal and distal parts define apertures at the second longitudinal axis, so that the guide tube may extend through the proximal and distal parts along the second longitudinal axis. Usually, the first and second axes will be parallel or at least substantially parallel when the fixator is positioned in the blood vessel.

When forcing the distal and proximal parts toward each other from the second to the first position, the cross section circumscribed by the deformable portion increases. This cross section may be the cross section at one position along (in a plane perpendicular to) the longitudinal axis or may be a mean cross section along the longitudinal axis over the length or extent of the deformable portion or central portion.

Usually, when positioned in the blood vessel, the expansion of the deformable portion is limited by the blood vessel. Outside the blood vessel, the expansion usually can take place for the deformable portion to reach cross sections larger than that of the blood vessel diameter or type for which the deformable portion or fixator is intended.

In a preferred embodiment, the preventing means prevent the distal part from travelling beyond the distal end. In this respect, the proximal part preferably is movable in relation to the distal part, the central portion and the guide tube, so that the pulling force is exerted to the distal part, which may, in the above fixator, cause the deformable portion to attempt to obtain a larger cross section and thus engage the blood vessel with a higher gripping force. The reason for this is that the attachment of the deformable portion to the blood vessel will act to have the pulling force actually force the distal part toward the proximal part which is more fixed in relation to the blood vessel. Thus, as the grip or engagement increases when the guide tube is pulled, the force with which the deformable portion engages the blood vessel, when no or only little force is exerted, may be low or weak, which causes less damage to the vessel walls.

However, due to the fact that the pulling force in this situation acts between the distal part and the central portion, the central portion will typically react by trying to increase the cross sectional area the most at the most distal parts. This increase is counteracted by the blood vessel wall, whereby a larger force is exerted thereto. This may not be desired, and different manners exist of counteracting this effect.

In one situation, the central portion has a rest shape that:
circumscribes a first cross sectional area in a plane perpendicular to the second longitudinal axis and at a first position along the second longitudinal axis and
circumscribes a second cross sectional area in a plane perpendicular to the second longitudinal axis and at a second position along the second longitudinal axis,
wherein the second position is closer to the distal part than the first position, the second cross sectional area being smaller than the first cross sectional area.

In this context, a rest shape is the shape which the central portion has when no forces act on it (except possibly gravity), including forces acting to force the distal and proximal parts toward each other, such as when the central portion is positioned on a table or horizontal surface.

Also, in this context, the first cross sectional area is at least 2%, such as at least 5%, preferably at least 7%, such as at least 10%, preferably as at least 15%, such as at least 20%, preferably at least 40%, such as at least 60% larger than the second cross sectional area.

When this fixator is positioned in the blood vessel, the central portion may or may not attach to the inner surface of the blood vessel at the second position with the smaller cross sectional area, when no or a small pulling force is exerted. However, when a pulling force is applied to the guide tube, the lower cross sectional area at the second position preferably acts to increase in size and/or have a more even force exerted to the blood vessel along the length or area of the deformable portion or the central portion. As described above, the pulling of the distal part primarily acts to increase the cross sectional area at positions closer to the distal end.

Preferably, the second position is a position within or at a distance of at the most 80%, such as at the most 60%, preferably at the most 40%, such as at the most 25%, preferably at the most 10%, such as at the most 5%, preferably at the most 2% of an extent of the central portion or the deformable portion along the second axis, from the distal end of the central portion.

In another situation, the central portion is adapted to, when the proximal and distal parts are forced toward each other along the second longitudinal axis:
circumscribe a third cross sectional area in a plane perpendicular to the second longitudinal axis and at a third position along the second longitudinal axis, and,
circumscribe a fourth cross sectional area in a plane perpendicular to the second longitudinal axis and at a fourth position along the second longitudinal axis, wherein the third position is closer to the distal part than the fourth position, the third cross sectional area being smaller than the fourth cross sectional area.

As mentioned above, the cross sections of the deformable portion or central portion will be limited by the blood vessel. Thus, this situation is normally seen when the fixator is outside the vessel and not limited in that manner.

When the proximal and distal parts are forced toward each other with the above-mentioned at least 0.1N, such as 0.2N, preferably 0.3N, such as 0.4N, preferably 0.5N, such as 0.6N, preferably 0.7N, such as 0.8N, preferably 0.9N, such as 1N, preferably 1.5N, such as 2N, preferably 2.5N, such as 3N, preferably 3.5N, such as 4N, preferably 5N, it will expand (obtain a larger cross sectional area) more at the fourth position and thus not at the distal part. As indicated above, preferably, the third position is a position within or a distance of at the most 80%, such as at the most 60%, preferably at the most 40%, such as at the most 25%, preferably at the most 10%, such as at the most 5%, preferably at the most 2% of an extent of the central portion or the deformable portion along the second axis, from the distal end of the central portion.

In general, the deformable portion may comprise a wire mesh or braided wires. The wire density of the deformable portion preferably is between 0.1 and 15 wires per mm, such as between 0.2 and 5 wires per mm, preferably between 0.5 and 3 wires/mm along the longitudinal direction. Also, the wire thickness may be between 0.01 mm and 1 mm, between 0.05 mm and 0.5 mm, preferably between 0.07 mm and 0.2 mm.

In a preferred embodiment, 40 wires (0.1 mm diameter) are used in a braid having a maximum diameter of 7 mm over a length of 14 mm when expanded and which, in the non-expanded shape, has a length of 40 mm.

In one situation, the wire mesh/braid has a wire density of the wire mesh/braid being higher at one of the second position, the third position, and a distal end of the central portion, than at one of the first position, the fourth position, and a proximal end, of the central portion. In this situation, the higher wire density (number of wires per distance unit along the second axis) will make the expansion (increase in cross sectional area) lower than where the wire density is lower; the higher wire density makes the pertaining parts of the deformable portion more stiff.

An alternative to or in addition to the wire density difference, the deformable portion may comprise a wire mesh/braid, wherein a wire thickness of the wire mesh/braid is higher at one of a the second position, the third position, and a distal end of the central portion, than at one of the first position, the fourth position, and a proximal end of the central portion. This wire thickness increase will also make the pertaining part stiffer.

A further alternative or addition is one comprising a circumference limiting element at one of the second position, the third position, and a distal end of the central portion. In this manner, the circumference and thus cross sectional area at the third position may be limited so as to exert only a predetermined force to the blood vessel. Any pulling of the guide tube will thus direct the force to other parts of the deformable portion further toward the proximal portion.

In an interesting embodiment, the guide tube comprises multiple lumens, the pump being adapted to transport liquid to/from the blood vessel via a first of the lumens, and wherein at least two lumens open, at the distal end, up toward the blood vessel at different longitudinal positions along a longitudinal direction of the guide tube at the distal end.

When multiple lumens are provided, one may be used for transporting the liquid to the blood vessel, and another may be used for transporting liquid from the blood vessel. When providing this transport to/from the vessel, the liquid added to the blood stream may be added at a position from which it flows to a position of interest in the blood vessel and from which blood will flow toward the position from which the sample is derived.

In another embodiment, the most upstream distal opening may be used for adding a drug to the blood flow to a down stream position of interest, where another drug, such as for converting or inactivating the first drug, is then added further downstream, downstream of the position of interest.

Alternatively or additionally, one lumen may be used for introducing a camera or the like for visual inspection of the blood vessel.

A second aspect of the invention relates to a method of providing a liquid to a blood vessel of a body or removing liquid from the blood vessel, the method comprising:
  providing a fixator connected to a distal end of a guide tube also having a proximal end,
  positioning the fixator and the distal end within the blood vessel so that the proximal end is positioned outside the body,
  introducing a liquid into the blood vessel or withdrawing liquid from the blood vessel via the guide tube while allowing blood flow in the blood vessel.

In this context the allowing of blood flow during introducing/withdrawal may be obtained as described in relation to the first aspect.

A number of manners exist for positioning an element into a blood vessel. One may be to puncture the blood vessel at the desired position. Other manners include more invasive steps, such as surgery.

Preferably, the positioning step comprises introducing the fixator and distal end into a second blood vessel of the body and guiding the fixator and distal end to the blood vessel via the second blood vessel and optionally additional blood vessels. This procedure, often called catheterizing, is often performed by entering the elements via a puncture in a femoral artery, such as when positioning stents or grafts in stenotic arteries around the heart or in the brain, for example.

The same method may be used for introducing the present fixator and distal end inside the blood vessel, and the method has the advantage that the fixator and distal end may remain dwelling inside the person and blood vessel for prolonged periods of time, as the blood flow is allowed at least to a certain degree in the blood vessel so that no organs or the like are damaged.

In one embodiment, the introducing/withdrawing step is performed intermittently over time. In another embodiment, the introducing/withdrawing step is performed constantly.

One embodiment may be one in which the introducing/withdrawing is performed by operation of a pump. Naturally, this step may also be dependent on or controlled by other factors, such as a result of an analysis of an earlier sample taken from the person.

In one embodiment, the introducing/withdrawing step, intermittent, continuous or other, is performed over a period of time of at least 10 minutes, such as at least 1 hour, such at least 4 hours, preferably at least 12 hours, such as at least 1 day.

An interesting embodiment is one which further comprises the step of providing a camera through the guide tube from the proximal end to the distal end and providing image data from the blood vessel at the distal end. This camera may be provided through a lumen in which liquid is or has been transported by the pump, such as when the pump is not operating, or through another lumen of the guide tube.

Embodiments of the invention will now be described with reference to the figures in which:

FIG. 1 is a schematic illustration of a fixator for use in a first embodiment of the invention, when disconnected from a retrieving catheter and with a delivery catheter retracted from the fixator;

FIGS. 2 and 3 are schematic illustrations of the fixator in FIG. 1 in different situations of use;

FIG. 5 is an exploded view of the fixator in FIG. 4;

FIG. 6 illustrates a third embodiment of a fixator;

Figure 13:
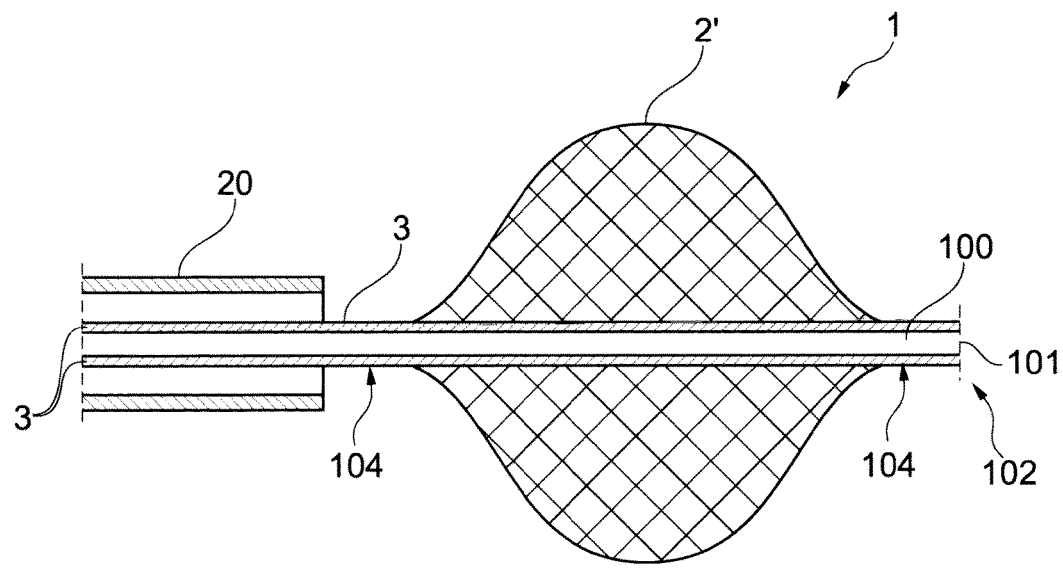
Figure 14:
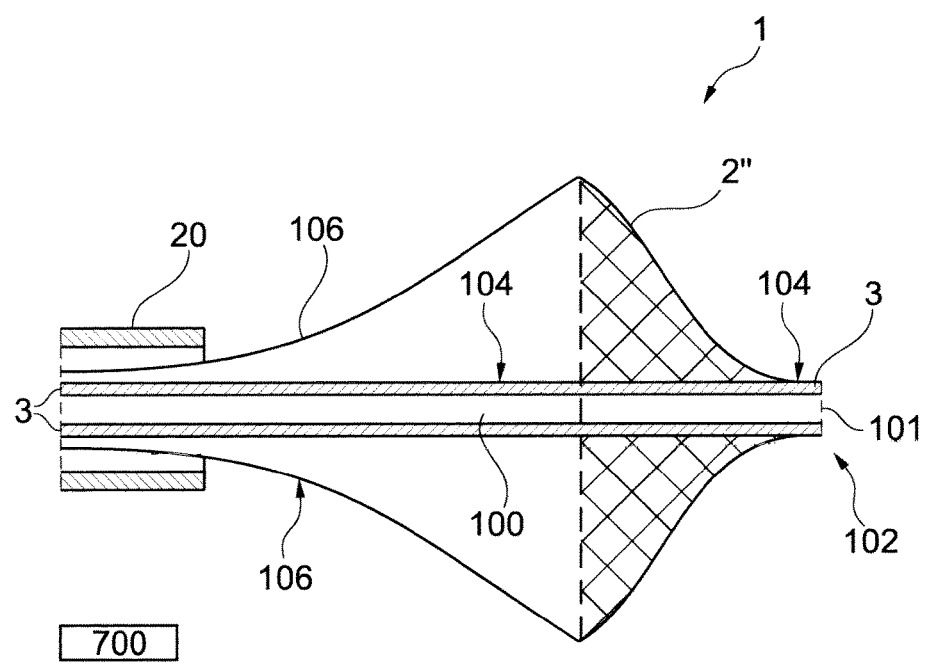
Figure 15:
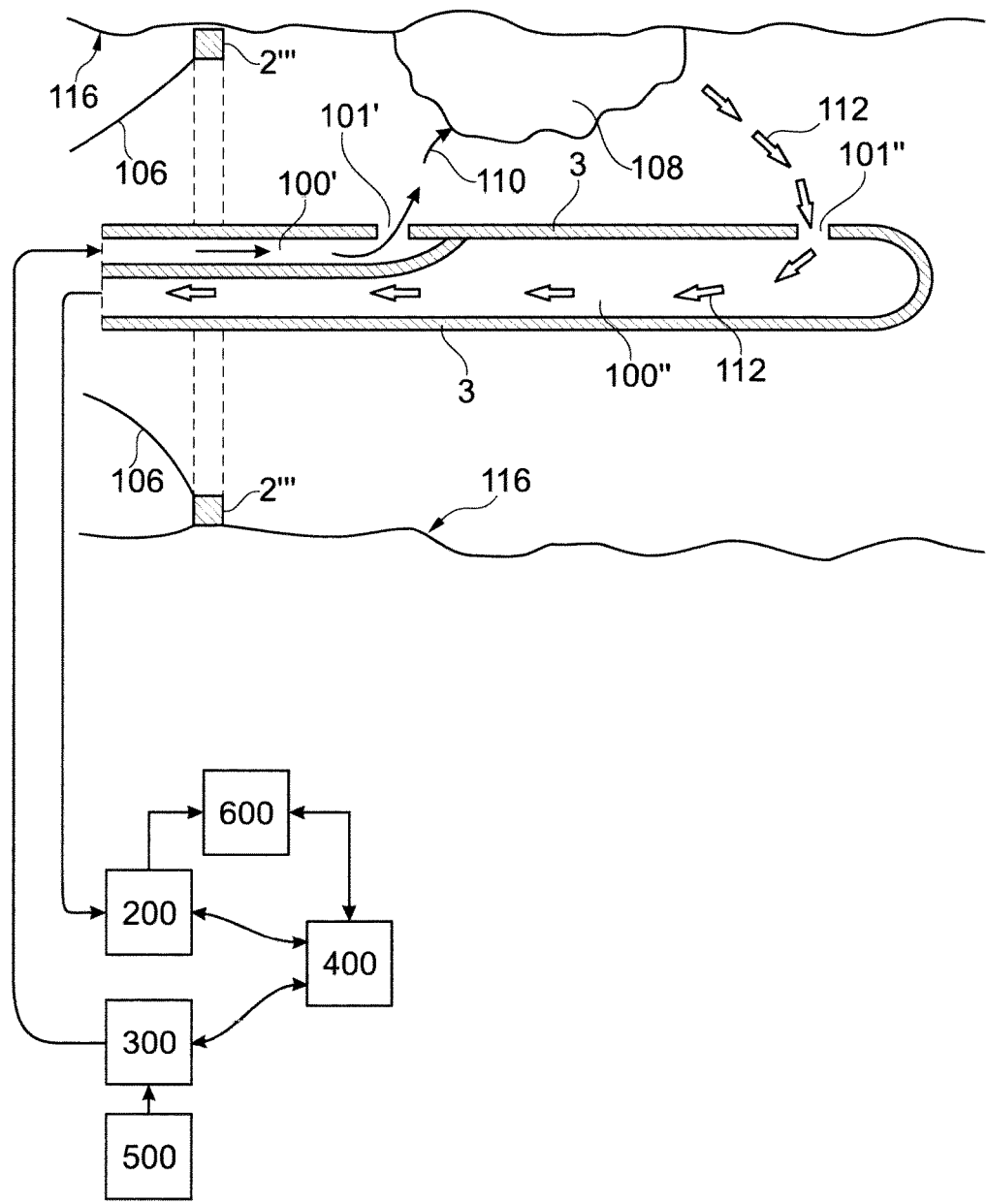

FIGS. 13-15 disclose the hollow guide tube.

In the below description of the figures, only FIGS. 13-15 disclose the hollow guide tube 3, however it shall be appreciated that any of the guide tubes 3 in the drawings shall be seen as hollow and adapted to dispense a medicament or to take a blood sample, however for simplicity reasons, the hollow tube 3 is only disclosed in FIGS. 13-15.

In the following description, the terms "distal" and "proximal" are used to denote the respective location of two corresponding parts, wherein the heart is used as reference, such that anatomical structures that are closer to the heart are denoted as proximal and details that are farther from the heart are denoted as distal. For parts of a medical device, such as the present fixator, the definition is instead based on the surgeon as reference. Hence, details that are closer to the surgeon are denoted as proximal and details that are farther from the surgeon are denoted as distal.

In FIG. 1, a first embodiment of a fixator 1 is shown. The fixator involves a flow transparent retainer or fixator 2, which in the shown embodiment consists of a metal frame basket. By flow transparent shall be understood that a fluid such as blood may flow through the basket when it is retained in the cardio vascular system.

The fixator 2 is arranged on a guide tube 3, which is adapted to serve two purposes. Firstly, it is used to for fixating the fixator 2 to a predetermined position in the blood vessel. Secondly, it may be used for dispensing a medicament or for taking blood samples inside the cardio vascular system, as is described below.

The guide tube 3 defines a conduit 100 extending longitudinally along the length of the guide tube 3. The conduit 100 may define a passage or canal defining one or more distal orifices 101 which are defined in the distal end 102 of the guiding tube 3 and one or more proximal orifices (not shown) which are defined in the proximal part of the guide tube. One or more of the orifices may extend between the conduit of the guide tube and an outer surface 104 thereof.

In cases where a medicament is administered by means of the guiding tube 3, the medicament may flow out through the distal orifices 101 which in this case serve as an outlet. In cases where a blood sample is taken by means of the guiding tube, the distal orifices 101 serves an inlet through which blood flows from the blood vessel into the conduit of the guiding tube.

One advantage of providing a hollow conduit 100 is the ability to dispense a medicament in a treatment area. If the medicament is dispensed to the cardio vascular system in the conventional way i.e through a travenous cannula inserted into a blood vessel of a hand, chances are that the medicament passes through the liver prior to reaching the treatment area, depending on the location of the treatment area relative to the device according to the present invention. This may result in the medicament being deteriorated or even inactivated by the liver, whereby the desired effect of the medicament is not obtained in the area of treatment by the medicament. By administrating a medicament through the conduit 100 to or in the vicinity of the treatment area, the medicament may be dispensed close where it is supposed to treat the human body.

Moreover, as the fixator is adapted to allow blood to flow there-through, the medicament may be dispensed over a longer periods of time as energy and oxygen will continue to flow in the downstream direction relative to the fixator.

Another advantage of providing the hollow conduit 100 is that it may be used to take blood samples from the blood at predetermined positions or in predetermined areas of the cardio vascular system.

Yet another advantage of providing a hollow conduit 100 is that diagnostic tools may be inserted into the cardio vascular system. One such example is diagnostic imaging devices 700, which once inserted may be used for diagnostic purposes. As an example, it may be used to determine the exact location of a tumour or to identify the effects of a treatment.

It will be appreciated that once the fixator has been fixed in the blood vessel, the hollow tube may be used for different purposes. As an example a medicament may be dispensed through the hollow tube and after a predetermined period of time a diagnostic imaging device may be inserted to determine the effect of the treatment. If the treatment has not resulted in the desired effect, the treatment may be continued and at a later stage the diagnostic imaging device may be used again to determine the effect at this later stage.

In use, the fixator 2 may be inserted into the blood vessel and fixated at a position upstream the treatment area, such that when the medicament is dispensed it flows downstream relative to the fixator 2 and towards the treatment area.

In cases where the guiding tube 3 is used to take samples e.g. blood samples, the fixator 2 may be retained at a position downstream a predetermined position in a blood vessel. This ensures that substances which are released into the blood from e.g. a tumour may be sampled immediately after their point of release (i.e. the tumour). This ensures that the substances are not diluted during their flow in the blood vessels.

In FIG. 1, a distal tubular sleeve 5 is arranged at the distal end 2a of the fixator. The distal sleeve 5 is fixed to the guide tube 3, whereas the proximal end 2b of the fixator 2 is arranged to slide over the guide tube 3 by means of a proximal tubular sleeve 4. The proximal and distal sleeves 4 and 5 jointly limit the possible deformation of the fixator 2 as its ends 2a and 2b are forced toward each other, which will be described below. The distal end 2a of the fixator 1 comprises a distal end part 6, which may be a continuation of the guide tube 3, and which is soft and pliable in order not to cause damage in the target vessel. Guide tubes 3 for catheterisation are typically of the dimensions between 0.14 and 0.89 mm in circumference. These are very pliable and atraumatic with a hydrophilic slippery surface that allows catheterisation of small, stenotic and kinked arteries, without damage to the target vessel wall.

The proximal end 2b of the fixator 2 involves a connecting member 7 for connecting the fixator 2 to a retrieving catheter 10. In the shown first embodiment, the connecting member 7 has internal threads that are arranged on the inside of the proximal tubular sleeve 4. The retrieving catheter 10, on the other hand, comprises a corresponding connecting member 11 in the form of external threads for mutual connection of the retrieving catheter 10 and the fixator 2.

In general (see FIG. 10), the fixator or deformable portion 2 has a central portion C, which attaches to or engages the vessel when deployed, and which is connected to the sleeves 4/5 via the end portions 2a and 2b.

Preferably, the fixator 1 also has or is supplied with or inside a delivery catheter 20 in the form of a hose of a diameter adapted to house the fixator 2 and the retrieving catheter 10. The delivery catheter 20 enables the positioning of the fixator 2 as it allows the fixator to be fully housed therein during the introduction and positioning of the fixator 1. It would however also be possible to keep the fixator collapsed without housing it inside a delivery catheter 20, e.g. by keeping the sleeves separated from each other by means of e.g. a screw controlled arrangement.

The length of the guide tube 3, the retrieving catheter 10 and the delivery catheter 20 must be sufficient to allow their respective proximal ends to be accessible to and manoeuvrable by the surgeon when the corresponding distal ends are located in a target vessel. Typically, the guide tube 3, the retrieving catheter 10 and the delivery catheter 20 all have lengths between 0.5 and 2.8 meters.

The function of the fixator 2 will be described step by step in an exemplary mode of use and with reference to FIGS. 2-4. A further description is found in relation to FIGS. 13-16.

In a first step, as shown in FIG. 2, the delivery catheter 20 is inserted into a target vessel 30, defined by a vessel wall 31 and an opening 32 into e.g. the aorta. During the insertion of the fixator 1, only the pliable distal end part 6 of the fixator 1 extends outside of the delivery catheter 20. The fixator 2 is undeployed or collapsed in the radial direction such that it fits inside the delivery catheter 20. In order to allow for the radial collapse, the fixator 2 is extended in the axial direction with the distal sleeve 5 at a relatively large distance from the proximal sleeve 4. During the insertion, the connecting member 7 of the fixator 2 is connected to the connecting member 11 of the retrieving catheter 10. The insertion of a catheter into an unblocked vessel is in itself conventional and is therefore not described in detail in this application.

In a second step, when the delivery catheter 20 is located inside the target vessel 30, the fixator 2 is pushed out from the inside of the delivery catheter 20. The pushing of the fixator 2 is achieved by means of mutual movement of the delivery catheter 20 on the one hand, and the retrieving catheter 10 on the other hand. As the fixator 2 exits the delivery catheter 20 it strives to regain its original shape, which is individually adapted to the diameter of the vessel 30 such that it exerts a certain pressure on the vessel wall 31. This pressure should be as low as possible in order not to harm the vessel, but it must however be sufficient to keep the fixator from moving with respect to the vessel. The fixator 2 has a flow transparent form that allows nutritive blood flow through it. In the present embodiment, the fixator 2 comprises crosswise woven threads, which are adapted to expand to a diameter that is slightly larger than an inside diameter of the relevant blood vessel so as to exert a pressure on the blood vessel wall that restrains the fixator 2 from moving with respect to the target blood vessel 30. The blood flow is allowed to flow through the crosswise woven threads.

Even though it is possible to provide the fixator 2 with means for obtaining the expanded shape, it is preferred that the fixator, and here the crosswise woven threads, has an expanded rest shape, so that the expansion merely is a movement toward the rest shape. This type of fixator may be obtained by providing the threads in the desired, expanded shape and heat treating the threads to have or give this expanded shape the rest shape.

Figure 3:
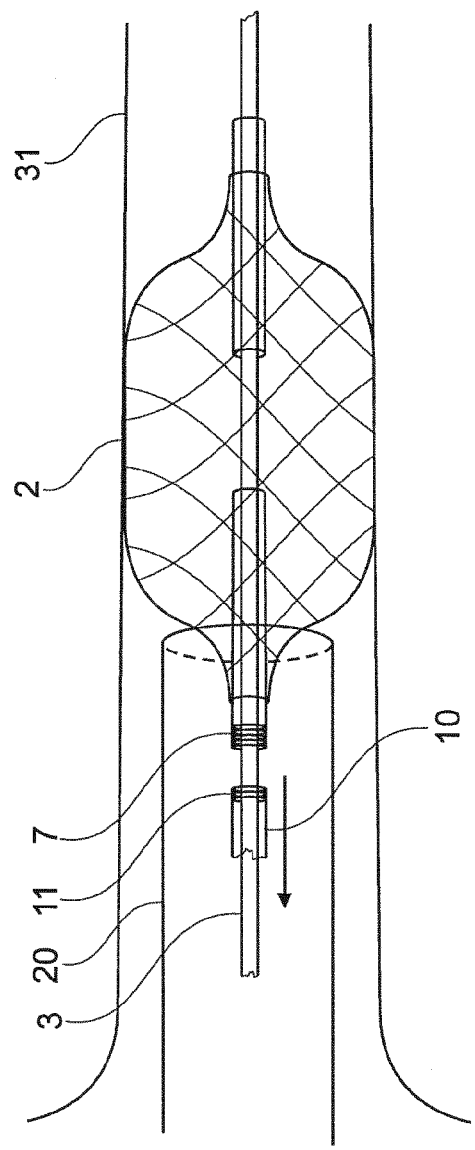

A third step, where the fixator 2 is fully deployed outside the delivery catheter 20 and at location inside the target vessel, is illustrated in FIG. 3. In this third step, the retrieving catheter 10 is disconnected from the fixator 2. In the present embodiment, this disconnecting is achieved in that the retrieving catheter 10 is rotated with respect to the fixator 2, which is restricted from rotating due to its contact with the vessel wall 31, such that the connecting member 11 of the retrieving catheter 10 is unscrewed from the connecting member 7 of the fixator 2.

In a fourth step, when the retrieving catheter 10 has been disconnected from the fixator 2, both the retrieving catheter 10 and the delivery catheter 20 may be withdrawn from the target vessel and leaving only the fixator 2 and the guide tube 3 in the vessel 30. The fixator 2 is arranged to not hinder the blood flow through the vessel.

In order to ensure that the fixator 2 is not disconnected from the guide tube 3 when the guide tube 3 is pulled, the proximal sleeve 4 and/or the distal sleeve 5 is releasably fixed to the guide tube 3, such as via a threaded connection, a snap fit or the like.

Figure 4:
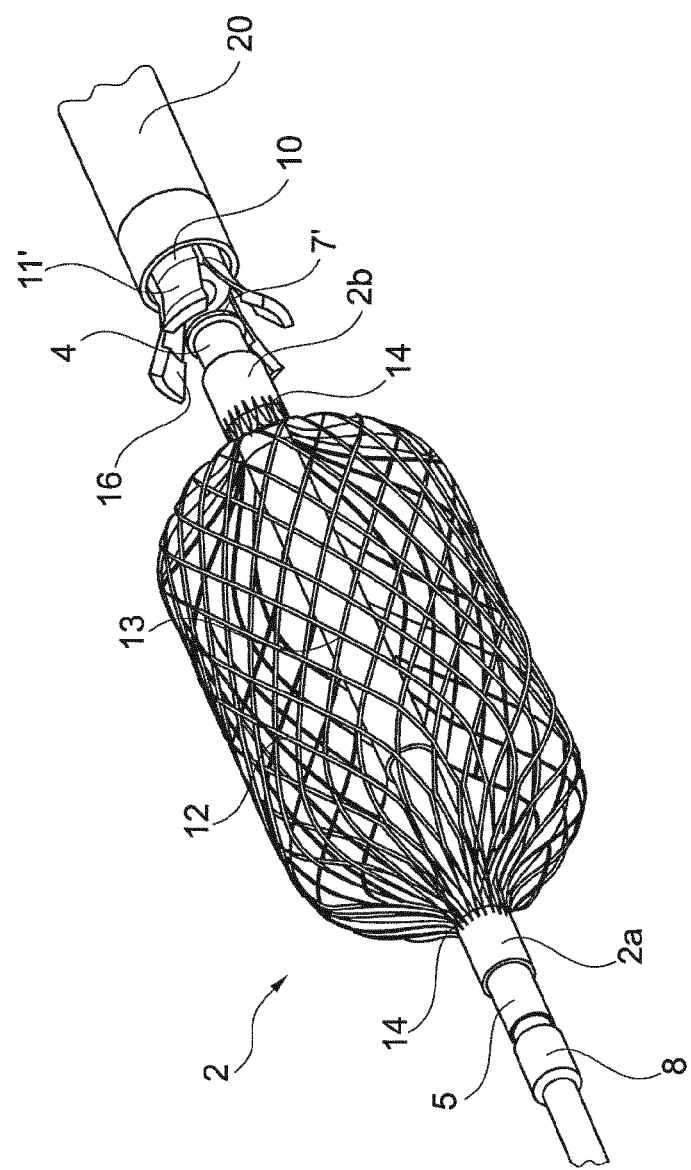
FIG. 4 illustrates a second embodiment of a fixator.

FIG. 4 illustrates a second embodiment of a fixator.

Naturally, details corresponding to details of the first embodiment are denoted with the same reference numerals, whereas details that are different from details of the first embodiment but that have the same function are denoted with the same reference numerals with an added apostrophe. A number of differences exist both in construction and use of the first and second embodiments. It is clear that such features may be interchanged between the embodiments if desired.

In the second embodiment of the fixator 1, the threaded attachment between the proximal sleeve 4 and the retrieving catheter 10 of FIG. 1 is replaced by a snap-on lock, including a connecting member 11' on the retrieving catheter 10 in the form of a claw like grasping unit with claws or projections 16 and a corresponding connecting member 7' in the form of a ring shaped stopper on, or in connection to, the proximal sleeve 4. The shape of the projections 16 is adapted to interlock with the ring shaped stopper as the connecting member 11' is retracted into the delivery catheter 20, and as the delivery catheter 20 is pushed over the connecting member 11'. Thus, the delivery catheter forces the projections to grasp over the connecting member when the fixator is retracted towards the retrieval catheter by the guide tube.

In FIG. 4, individual threads/wires 12 of the basket shaped fixator 2 are clearly visible. The threads/wires 12 may be welded together at crossing points 13, or they may be braided such that they pass each other by turns over and under each other. The ends 14 of the threads are securely fastened to the sleeves 4 and 5, respectively, either by welding, gluing or sewing or in any other suitable manner. Further, in FIG. 4, the connecting member 7' in the form of the ring shaped stopper may be seen inside the claw like grasping unit that constitutes the connecting member 11' on the retrieving catheter 10.

In the second embodiment, both sleeves 4 and 5 are arranged to slide over the guide tube 3. However, a stopper 8 positioned on the guide tube 3 prevents the sleeves from moving over the distal end of the guide tube 3 and thus disconnect fully from the guide tube 3.

Alternatively, the distal sleeve 5 may be detachably fixed, using e.g. any of the fastening methods between catheter 10 and sleeve 4. The reason for this detachability or slidability will be described further below.

Further, from this view it is apparent that the function of the sleeves is somewhat different in this embodiment with respect to their function in the first embodiment. In this embodiment, the connecting member 7' is arranged directly on the proximal sleeve 4 of the fixator. The proximal sleeve 4 is partly and fixedly housed inside a protective sleeve 15 (see also FIG. 5), which extends inside the basket shaped fixator 2 and also partly houses the distal sleeve 5. When the fixator 2 is in its deployed shape, there is a gap between the distal and the proximal sleeves 5 and 4, respectively. As the guide tube 3 is pulled, or the fixator 2 is allowed to expand toward its rest shape, the fixator 2 is fixed to the vessel wall, and any pulling force applied to the distal sleeve 5 will thus act to compress the fixator in the axial direction. Thus, the sleeves move closer to each other, until the proximal end 5b of the distal sleeve 5 reaches the distal end 4a of the proximal sleeve 4. The contact between these ends of the sleeves thus limits the axial deformation of the fixator 2. The distal end 5a of the distal sleeve 5 is arranged to interact with the stopper 8 on the guide tube 3 and limit the axial movement of the guide tube 3 with respect to the fixator 2, as described above.

In a third embodiment the guide tube 3' is a hypotube, as is shown in FIG. 6. The hypotube may be made of Nitinol or stainless steel and is preferably coated by a hydrophilic coating, such as e.g. PTFE, in order to create a slippery contact surface to the retrieving catheter 10. The hypotube may be just as flexible as a guide tube, or more flexible. The suitable size of a hypotube may range from 0.5 mm to about 2 mm with a wall thickness of about 0.04 to 0.2 mm.

Preferably, the hypotube should have a sufficiently large inner diameter to successfully house a stiff conveying wire 25. The stiff conveying wire 25 is helpful for guiding the insertion of the fixator 1. In order for the guide tube 3' to be rerouted, it has to be flexible and pliable. However, due to the pliability of the guide tube 3', it may be difficult to control the guide tube 3' and to guide it into the target blood vessel. Hence, the stiff conveying wire 25 will make it possible to control the guide tube 3' during insertion. The conveying wire 25 enables the insertion of further catheters and or stent branches on the guide tube. With a stiff conveying wire inside the guide tube 3', the stent graft branch can be introduced over the stiff conveying wire 25, either directly over the conveying wire 25 or over the (hypo-) tubular guide tube 3' housing a conveying wire.

The stiff conveying wire 25 may be withdrawn from inside the guide tube 3' when the fixator 2 has been located in the target vessel 30. When the stiff conveying wire 25 has been withdrawn from inside the guide tube 3', the guide tube is sufficiently pliable and flexible to be rerouted inside an arterial system in an atraumatic manner.

The guide tube 3' may be provided with an opening 26 near its distal end. With such an opening 26 the guide tube 3' may constitute a conduit for locally distributing a pharmaceutical via said opening 26. In many situations, e.g. when treating tumours, it is of interest to deliver a pharmaceutical agent locally, especially since certain pharmaceuticals, although effectively treating a disease process at one location, may be harmful if distributed systematically. Until now there has been no reliable way of delivering a pharmaceutical endovascularily over a period of time.

By means of a guide tube 3' in the form of a hypotube comprising a fixator 2 it is possible to fix the end of the hypotube inside a target vessel and to deliver a desired amount of a pharmaceutical through the opening 26 at the desired location, without risking that the hypotube will move and lose this location.

Naturally, the fixator of FIG. 6 may, for most parts, be similar to the fixator according the first and second embodiments. For example, a stopper 8 may be provided on the guide tube 3' for interaction with the distal sleeve 5, and a protective sleeve 15, which extends inside the basket shaped fixator 2, is arranged to partly house the distal sleeve 5. Further, the distal end 6 of the guide tube 3' is preferably soft and pliable in order not to cause damage inside the body. Also, the proximal part of the guide tube 3', e.g. proximal to the fixator 2, is also pliable in order to allow rerouting. In a conventional manner, the tip of the guide tube 3', may include a 180° bend (not shown) that prevents arterial damage in the target vessel.

Figure 7:
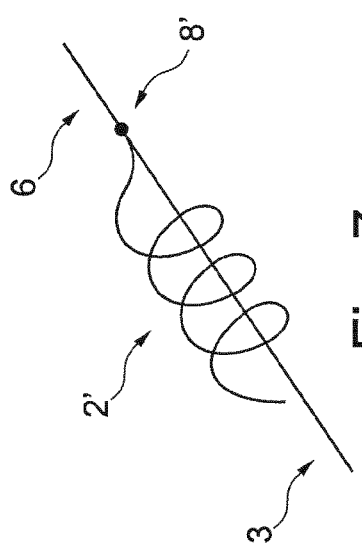
FIG. 7 illustrates a fourth embodiment of a fixator.

FIG. 7 illustrates a fourth embodiment of a fixator 2'. This fixator 2' has the shape of a helical spring and is still releasably fixed to the guide tube 3 with a stopper 8'. The distal end of the fixator 2' may have a ring-shaped element through which the guide tube 3 extends and which engages with the stopper 8' to prevent the fixator 2' from moving over the distal end of the guide tube 3. This fixator 2' has the advantage of being extremely simple in manufacture as well as presenting very little flow resistance in the blood vessel.

Introduction and retraction of the fixator 2' may be performed using a catheter. Withdrawing the pre-formed fixator 2' will simply rotate this without scraping or damaging the vessel wall.

In the present embodiments the fixator 2/2' preferably comprises a metal structure of weaved, coiled and/or braided wires or threads, preferably from Nitinol. Other biocompatible materials with similar properties may also be used, e.g. other alloys or plastics. The material must be sufficiently flexible to allow it to be collapsed without being plastically deformed, but at the same time sufficiently rigid to exert a pressure when released inside a vessel. In a specific method of producing the fixator 2/2', a Laser cut length of a braided Nitinol tube is drawn around a template of a desired shape. The ends of the Nitinol tube are shrunk around the ends of the template and a heat treatment is performed in this position, such that the Nitinol basket, i.e. the fixator, adapts to this new shape. The fixator will then strive to regain this shape whenever unaffected by exterior forces.

Alternative fixators 2/2' may have a larger general contact area with the blood vessel, such as when using a piece of cloth, material or the like, which is supported on the coiled spring or the braided wire so as to better even out or enlarge the actual contact surface between the fixator and the blood vessel wall.

As will be described in more detail below, the advantageous arrangement of the above embodiments enables the fixator to remain in place as the guide tube 3 is subject to tension, e.g. from rerouting of its proximal end. The proximal sleeve 4 is arranged to slide on the guide tube 3 such that it remains unaffected by it, whereas the distal sleeve 5 is prevented from travelling toward the distal end of the guide tube 3. Due to this arrangement any pulling forces on the guide tube 3 will compress the fixator 2 in the axial direction, due to the friction between the vessel wall 31 and the proximal part of the fixator 2, such that the fixator 2 is expanded in the radial direction, see FIG. 8. Hence, the pressure against the vessel wall 31 will increase as a function of the pulling force on the guide tube, such that the increased friction force between the fixator 2 and the vessel wall 31 instantaneously increases with the increased pulling force. Therefore, by means of the increased friction force, the fixator 2 is kept in place.

This arrangement allows for the fixator to exert only a minimum force on the vessel wall 31 as long as it is unaffected by any pulling force, in order to minimise the traumatic effect on said vessel. Also, during most parts of a normal operational procedure, the guide tube is not affected by any forces at all. The function of the fixator 1 is mainly to retain the position inside the target vessel. Pulling forces normally only arise when the guide tube 3 is being rerouted. The axial compression of the fixator may be limited by interaction of the sleeves 4 and 5, as they come into contact with each other in response to a pulling force on the guide tube 3. Hence, the maximum radial extension of the fixator 2, and thus the maximal radial force exerted by it on the vessel wall, can be limited by the available distance between the sleeves; the greater the distance, the greater the possible axial compression and consequent radial extension.

Figure 8:
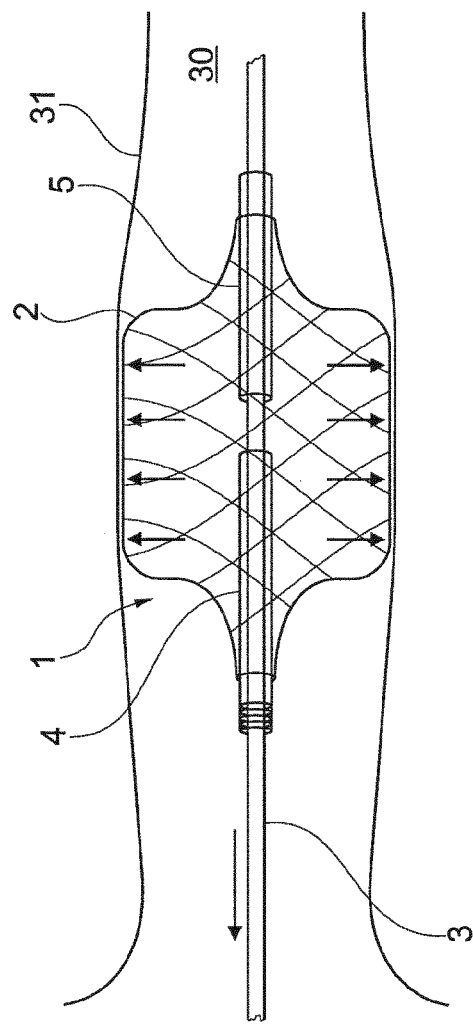
FIG. 8 illustrates the force exertion during attachment to the blood vessel.
Figure 9:
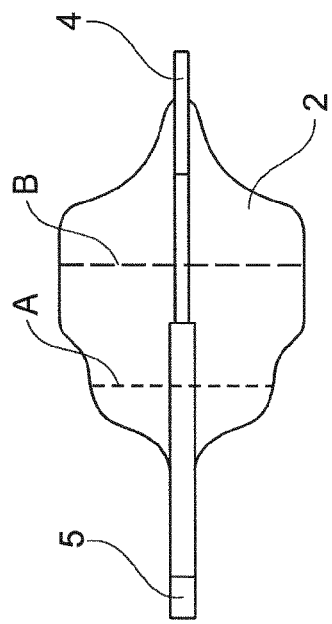
FIG. 9 illustrates the force exertion outside the blood vessel.

It has been found, however, that even though, as is seen in FIG. 8, the fixator 2 is bounded perpendicular to its longitudinal axis, of the dimensions (primarily thickness or radius) of the blood vessel 30, there may be a difference along the longitudinal direction of the force exerted to the blood vessel. The cause is that as the fixator or deformable portion 2 engages the vessel wall 31 and the distal sleeve pulled, the force is not distributed evenly over the area engaged by the fixator 2 but mainly at the distal part thereof. In FIG. 9, the shape of a fixator 2 in an element more flexible than a blood vessel is illustrated. It is seen that the cross sectional area (or radius if circular or having rotation symmetry) at the longitudinal position A is larger than at position B which is positioned more proximal than A.

Figure 10:
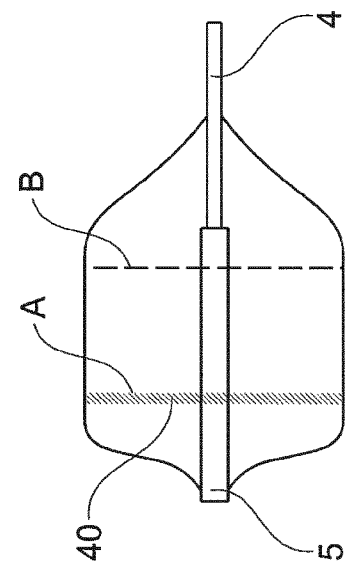
FIGS. 10-12 illustrate different embodiments of a deformable portion for the present fixator.
Figure 11:
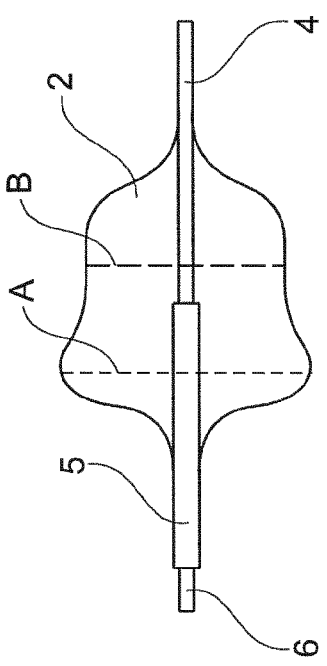
Figure 12:
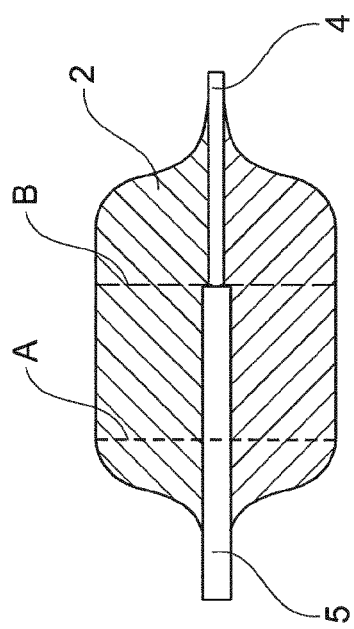

Thus, in order to distribute this force more evenly, different solutions are illustrated in FIGS. 10-12.

In FIG. 10, the fixator 2 has an asymmetric shape, when non-stressed and/or in a non-compressed state, over the longitudinal length which is to engage the blood vessel, where a part of the fixator 2 closer to the distal end or sleeve 5 has a smaller cross sectional area (or radius if circular or having rotation symmetry) at position A than closer to the proximal sleeve 4, such as at position B.

Thus, when positioned in the blood vessel 30 and without pulling the guide tube 3, the shape of the fixator 2 of FIG. 10 may look like in FIG. 8, where the force exerted to the wall 31 is uneven but still quite low. When the guide tube 3 is pulled, however, the increased force exerted on the wall 31 may be more even, as the more narrow rest shape of the distal part (around position A) of the fixator 2 will act to counter-act a large expansion and thus force increase at that part.

In FIG. 11, the rest shape or non-stressed/non-compressed shape of the fixator 2 may be symmetric but the expandability of the fixator 2 asymmetric along the longitudinal direction. In FIG. 11, the fixator 2 is provided as a wire mesh with a higher wire density at position A compared to position B. Thus, when compressing the fixator 2 outside the blood vessel 30, an asymmetric shape as that illustrated in FIG. 10 may be obtained. Also, when compressing the fixator 2 or pulling the guide tube 3 when the fixator 2 is deployed in the vessel 30, the higher wire density at position A will act to even out the pressure exerted and ensure that more force is applied around position B.

Naturally, the same functionality may be obtained by adapting the wire thickness or other parameters of the wire mesh.

In FIG. 12, another manner is illustrated which prevents excessive force exerting on the vessel 30 close to the distal end of the fixator 2. In this embodiment, a circumference limiting element 40 is provided at the distal end at position A. This element 40 prevents the circumference of the fixator 2 from exceeding a predetermined length, whereby any further deformation will be required at the more proximal parts, such as around position B. This circumference limiting element 40 may be a non-stretchable element, such as a band, a wire or the like.

In general, it is noted that different types of materials for the fixator 2 and different constellations thereof may be chosen. The overall functionality is that the fixator 2 should be able to engage the vessel wall while allowing a blood flow there through.

The fixator above may be provided in different sizes, e.g. 5, 6, 7, 8, 9, 10, 11, 12, 13 14 mm in diameter, or fractions thereof, for use in arteries of corresponding diameter. The collapsed fixator 2 diameter is typically 8 French (2.67 mm diameter on the French catheter scale), and may vary from about 6 to about 12 French (about 2 to about 4 mm), including sizes of 6, 7, 8, 9, 10, 11, 12 French and half sizes there between, depending on the diameter of the delivery catheter to be used to house the fixator. The size of the delivery catheter is accordingly also from about 6 to about 12 French (about 2 to about 4 mm), including sizes of 6, 7, 8, 9, 10, 11, 12 French and half sizes there between. The retrieving catheter has a size that allows it to fit outside the guide tube and inside the delivery catheter, e.g. from about 3 to about 10 French (about 1 to about 3.3 mm), including sizes of 3, 4, 5, 6, 7, 8, 9, 10 French and half sizes there between. Usually, the guide tube and/or the hypotube guide tube is very pliable and usually have a hydrophilic surface allowing catheterization of narrow, stenotic arteries without damage to the target vessel.

One embodiment of the fixator may be one made of 40 braided 100 μm diameter Nitinol wires provided as a, when compacted, 40 mm long element which may be used in e.g. 5-7 mm blood vessels. When expanded in a 5 mm blood vessel, this fixator will occlude about 58% of the blood vessel cross sectional area, and the openings seen by the blood when flowing through the fixator will be 0.015-0.18 mm$^2$, whereas the occluding percentage in a 7 mm blood vessel is about 47% and the openings 0.06-0.25 mm$^2$.

FIG. 13 discloses an embodiment of the fixator 2 in which the guide tube 3 defines a conduit 100 extending in the longitudinal direction of the guide tube 3. For simplicity reasons, the fixator is illustrated as being attached in both ends to the guide tube 3, however it will be appreciated that it may be secured to the guide tube 3 according to any of the preciously described embodiments. Accordingly, it may be secured to the guide tube 3 in one of the two ends, as is illustrated in FIG. 14.

In FIG. 14 the fixator 2 is expanded and contracted by loosening and tightening the wires 106 which are accommodated in the lumen of the delivery catheter 20. It will be appreciated that the two wires 106 may be secured to each other such that only one wire extends longitudinally inside the lumen of the delivery catheter 20 or a part thereof.

In the embodiments of FIGS. 13 and 14, the distal orifice 101 is provided at the end of the guide tube 3. However, they may also be provided in other positions such as at an outer surface 104'404" of the guide tube 3 as illustrated in FIG. 15.

In the embodiment of FIG. 15, the guide tube 3 is a bi-lumen tube defining a first conduit 100' and a second conduit 100". The first conduit 100' is fluidly connected to a first orifice 101', and the second conduit 100" is fluidly connected to a second orifice 101".

During use, the bi-lumen guide tube 3 may be inserted into the into a position wherein the first orifice 101' is positioned upstream relative to a treatment area e.g. a tumour 108 while at the same time the second orifice 101" is positioned downstream relative to the tumour 108. Accordingly, a medicament may be dispensed to the treatment area through the first orifice 101' (indicated by in single arrows 110) while at the same time samples may be taken by means of the second orifice 101" (indicated by double arrows 112). In some embodiments, this is done concurrently, while in other embodiments, the treatment is performed at a first point in time while the sample taking is performed at a later second point in time.

In FIG. 15 the fixator 2''' is provided in the form of a ring shaped member which may be moved between an expanded state and a collapsed state. In the expanded state, the ring shaped member 2''' abuts an inner surface 116 of the blood vessel, while in the collapsed state its radial dimension is smaller than when it is provided in the expanded state.

In FIG. 15, the pump 300 is illustrated which derives a liquid from a reservoir 500 and which may be controlled by a processor, PC, server, laptop, computer, controller or the like 400 which also receives information from an analyser 600 receiving liquid from a pump 200 deriving the liquid from the tube 3. The analyser 600 outputs analysis results to the processor 400, so that the processor 400 may operate the pumps and optionally the analyser 600 to perform a desired type of process, such as the dosing of liquid (operation of the pump 300) on the basis of the results of the analysis.

The invention claimed is:

1. An assembly, comprising:
    a guide tube having a distal end for introduction into a blood vessel and a proximal end;
    a fixator attached to the guide tube and configured to releasably attach to an inner side of the blood vessel, the fixator being configured to allow blood flow in the blood vessel during transport of liquid to or from the blood vessel, the fixator including
        a deformable portion having a central portion configured to attach to the inner side of the blood vessel at a length thereof, along a first longitudinal direction of the blood vessel,
        a distal part attached to the deformable portion, the distal part including a distal sleeve configured to slide relative to the guide tube, and
        a proximal part attached to the deformable portion, the proximal part including a proximal sleeve configured to slide relative to the guide tube;
    a pump configured to transport a liquid to the blood vessel through the guide tube or from the blood vessel through the guide tube; and
    a stopper fixed to the guide tube and configured to prevent the fixator from travelling distally beyond the stopper based on restricting the distal sleeve from sliding distally relative to the stopper,
    wherein,
        the fixator is configured to move toward the proximal end of the guide tube independently of the guide tube and unrestricted by the stopper, concurrently with the fixator maintaining attachment to the inner side of the blood vessel and based on the proximal sleeve and the distal sleeve sliding relative to the guide tube.

2. The assembly according to claim 1, wherein the deformable portion defines, when projected on to a plane perpendicular to the first longitudinal direction and in a rest position, a circumscribed portion with a first area and a cross section being less than 15% of the first area.

3. The assembly according to claim 1, wherein the deformable portion defines, when projected on to a plane perpendicular to the first longitudinal direction and in a rest position, a circumscribed portion with a first area.

4. The assembly according to claim 1, wherein the deformable portion defines, when projected on to a plane perpendicular to the first longitudinal direction and in a rest position, a circumscribed portion with a first area and wherein the fixator defines, when projected on to the plane and in the rest position, a cross section being less than 75% of the first area.

5. The assembly according to claim 1, wherein the deformable portion is adapted to exert at least substantially a common same force to the blood vessel along all of a particular length when a pulling force of at least 0.1N is exerted to the guide tube and fixator.

6. The assembly according claim 1, wherein,
    the central portion of the deformable portion circumscribing, in a plane perpendicular to a second longitudinal axis, a larger cross section when a first distance exists between the proximal and distal parts compared to when a second distance exists between the proximal and distal parts, the second distance being larger than the first distance.

7. The assembly according to claim 6, wherein,
    the central portion has a rest shape,
    the rest shape circumscribes a first cross sectional area in a particular plane perpendicular to the second longitudinal axis and at a first position along the second longitudinal axis,
    the rest shape circumscribes a second cross sectional area in a separate plane perpendicular to the second longitudinal axis and at a second position along the second longitudinal axis, and
    the second position is closer to the distal part than the first position, the second cross sectional area being smaller than the first cross sectional area.

8. The assembly according claim 6, wherein the central portion is configured to, based on the proximal part and the distal part being forced toward each other along the second longitudinal axis,
    circumscribe a third cross sectional area in a particular plane perpendicular to the second longitudinal axis and at a third position along the second longitudinal axis, and
    circumscribe a fourth cross sectional area in a separate plane perpendicular to the second longitudinal axis and at a fourth position along the second longitudinal axis,
    wherein the third position is closer to the distal part than the fourth position, the third cross sectional area being smaller than the fourth cross sectional area.

9. The assembly according to claim 6, wherein the deformable portion comprises a wire mesh, and wherein a wire density of the wire mesh is higher at the distal end, than at the proximal end.

10. The assembly according to claim 7, wherein the deformable portion comprises a tube mesh, and wherein a tube thickness of the tube mesh is higher at one of the distal end and the second position than at one of the proximal end and the first position.

11. The assembly according to claim 8, further comprising a circumference limiting element at one of the distal end, the second position and the third position.

12. The assembly according to claim 1, wherein the guide tube comprises multiple lumens, the pump being configured to transport liquid to or from the blood vessel via a first of the lumens, and wherein at least two lumens open, at the distal end, up toward the blood vessel at different longitudinal positions along a longitudinal direction of the guide tube at the distal end.

13. The assembly according to claim 1, wherein the proximal end of the guide tube is configured to remain outside of a body while the fixator is positioned in a blood vessel of the body.

14. The assembly according to claim 1, further comprising:
- a retrieving catheter and a delivery catheter, wherein the guide tube, the retrieving catheter and the delivery catheter have lengths of 0.5-2.8 m, respectively.

15. The assembly according to claim 1, wherein the fixator is configured to maintain attachment to the inner side of the blood vessel, based on a pulling force of at least 0.1N being applied to the guide tube and, via the stopper, to the fixator.

16. A method of providing a liquid to a blood vessel of a body or removing liquid from the blood vessel of the body, the method comprising:
- providing a fixator connected to a stopper at a distal end of a guide tube, the stopper fixed to the guide tube, the guide tube also having a proximal end, the fixator including
    - a deformable portion having a central portion configured to attach to an inner side of the blood vessel at a length thereof, along a first longitudinal direction of the blood vessel,
    - a distal part attached to the deformable portion, the distal part including a distal sleeve configured to slide relative to the guide tube, and
    - a proximal part attached to the deformable portion, the proximal part including a proximal sleeve configured to slide relative to the guide tube;
- positioning the fixator and the distal end of the guide tube within the blood vessel of the body so that the proximal end of the guide tube is positioned outside the body;
- detaching the fixator from the stopper, such that
    - the stopper prevents the fixator from travelling distally beyond the stopper, and
    - the fixator is configured to move toward the proximal end of the guide tube independently of the guide tube and unrestricted by the stopper, concurrently with the fixator maintaining attachment to the inner side of the blood vessel; and
- introducing the liquid into the blood vessel or withdrawing liquid from the blood vessel of the body via the guide tube while allowing blood flow in the blood vessel of the body.

17. The method according to claim 16, wherein the positioning includes introducing the fixator and distal end into a second blood vessel of the body and guiding the fixator and distal end to the blood vessel of the body via the second blood vessel of the body.

18. The method of claim 16, wherein the introducing or withdrawing is performed intermittently over time.

19. The method of claim 16, wherein the introducing or withdrawing is performed over a period of time of at least 10 minutes.

20. The method of claim 16, further comprising:
- providing a camera through the guide tube from the proximal end to the distal end and providing image data from the blood vessel of the body at the distal end.

* * * * *